US012797016B2

(12) United States Patent
Kosmeh

(10) Patent No.: US 12,797,016 B2
(45) Date of Patent: Nov. 17, 2026

(54) VIRTUAL HEALTHCARE APPARATUS, METHODS AND SYSTEMS

(71) Applicant: John Kosmeh, Rutherfordton, NC (US)

(72) Inventor: John Kosmeh, Rutherfordton, NC (US)

( * ) Notice: Subject to any disclaimer, the term of this patent is extended or adjusted under 35 U.S.C. 154(b) by 333 days.

(21) Appl. No.: 18/514,940

(22) Filed: Nov. 20, 2023

(65) Prior Publication Data

US 2024/0090855 A1 Mar. 21, 2024

Related U.S. Application Data

(60) Provisional application No. 63/376,315, filed on Sep. 20, 2022.

(51) Int. Cl.

| | |
|---|---|
| ***A61B 5/00*** | (2006.01) |
| ***A61B 5/0205*** | (2006.01) |
| ***H04N 7/18*** | (2006.01) |
| *A61B 1/227* | (2006.01) |
| *A61B 5/022* | (2006.01) |
| *A61B 5/145* | (2006.01) |
| *A61B 5/1455* | (2006.01) |
| *A61B 5/332* | (2021.01) |
| *A61B 7/02* | (2006.01) |
| *A61B 8/00* | (2006.01) |
| *H04L 67/12* | (2022.01) |
| *H04N 23/90* | (2023.01) |

(52) U.S. Cl.

CPC ........ *A61B 5/7465* (2013.01); *A61B 5/02055* (2013.01); *H04N 7/181* (2013.01); *A61B 1/227* (2013.01); *A61B 5/022* (2013.01); *A61B 5/14532* (2013.01); *A61B 5/14551* (2013.01); *A61B 5/332* (2021.01); *A61B 7/02* (2013.01); *A61B 8/565* (2013.01); *H04L 67/12* (2013.01); *H04N 23/90* (2023.01)

(58) Field of Classification Search

CPC ............................ A61B 5/7465; A61B 5/0004
USPC .......................................................... 600/301
See application file for complete search history.

(56) References Cited

U.S. PATENT DOCUMENTS

| | | | | |
|---|---|---|---|---|
| 11,031,106 | B2 | 6/2021 | Anvard | |
| 2004/0078220 | A1 | 4/2004 | Jackson | |
| 2016/0180026 | A1 | 6/2016 | Kim | |
| 2016/0188830 | A1 * | 6/2016 | Haq | G06Q 10/025 705/2 |
| 2018/0189452 | A1 * | 7/2018 | Serhani | G16H 50/20 |

(Continued)

FOREIGN PATENT DOCUMENTS

WO WO-2020201969 A1 * 10/2020 ........... H04N 23/695

OTHER PUBLICATIONS https://www.mckinsey.com/industries/healthcare/our-insights/virtual-hospitals-could-offer-respite-to-overwhelmed-health-systems.
https://www.ncbi.nlm.nih.gov/pmc/articles/PMC9047099/.
https://www.teladochealth.com/organizations/hospitals-health-systems/virtual-care-platform/?utm_source=google&utm_medium=paidsearch&utm_content=core-plt&utm_term=telehealth%20nursing&utm_campaign=2023fy-bas-dgn-psa&utm_id=hhs2/&gad_source=1&gclid=CjwKCAjwkY2qBhBDEiwAoQXK5fv0UMeb2Mjae0RSLStwaV248g8ISogDG5ltEyjGBWZm0QeEEkA0WhoCq6MQAvD_BwE.

*Primary Examiner* — Nicole F Johnson
(74) *Attorney, Agent, or Firm* — ArentFox Schiff LLP

(57) ABSTRACT

Apparatus, methods, and systems, of conducting virtual healthcare examinations of patients are provided by using a mobile workstation to collect video and/or audio from patients and other patient information using an integrated system of a plurality of cameras, an ultrasound machine, a 12 lead EKG unit, an otoscope, a thermometer, a blood glucose machine, a pulse oximeter, a blood pressure cuff, (Continued)

and a stethoscope and providing it to healthcare professionals and other interested persons who are not on site.

20 Claims, 4 Drawing Sheets

(56) References Cited

U.S. PATENT DOCUMENTS

| | | | | |
|---|---|---|---|---|
| 2018/0330815 | A1 | 11/2018 | Demir | |
| 2020/0405404 | A1 * | 12/2020 | Shelton, IV | A61B 18/00 |
| 2022/0051770 | A1 | 2/2022 | Barkol | |
| 2022/0230736 | A1 | 7/2022 | Sastry | |
| 2022/0319683 | A1 | 10/2022 | Wager | |

* cited by examiner

VIRTUAL HEALTHCARE APPARATUS, METHODS AND SYSTEMS

CROSS REFERENCE TO RELATED APPLICATIONS

This application claims the benefit of U.S. Provisional Application Ser. No. 63/376,315, filed on Sep. 20, 2022, which is hereby incorporated by reference herein in its entirety.

FIELD OF THE INVENTION

The invention relates to equipment, methods and systems for providing virtual healthcare.

BACKGROUND OF THE INVENTION

In the healthcare system, skilled nursing facilities and rural areas, among other locations, do not have ready access to certain medical equipment and healthcare professionals, including physician assistants and physicians, including specialists. Telemedicine connections in the form of simple telephone and video consultations have been used in the past, but they do not provide access to the medical equipment and results therefrom that may be needed and many do not have the ability to include patient family members and other healthcare professionals in a patient visit. Patients and the healthcare system would benefit from having access to more advanced equipment, family members, and healthcare professionals overall for a patient visit and treatment. Therefore, improved medical equipment, methods and systems are needed for remote and virtual patient visits and treatment.

SUMMARY OF THE INVENTION

Embodiments of this invention provide integrated virtual healthcare apparatus, methods and systems. These embodiments allow healthcare providers to remotely and virtually examine and treat patients and provide definitive medical diagnostic care in a wide variety of circumstances and provide much more than traditional telemedicine has been able to do.

These embodiments allow healthcare providers to gain a full picture of the patient with heart rate, blood pressure, oxygen saturation, temperature, long sounds, 12-lead EKG and ultrasound imaging, among others, which are often the results that a patient would need to go to an emergency room to receive. Additional embodiments provide pharmacy care, echocardiograms, full metabolic profiles (CBC), blood gas testing and an interface with cloud-based healthcare software providers (e.g., PointClickCare).

These embodiments may also be provided with the capability to facilitate the ordering of additional lab work, the calling in of prescriptions, arranging for follow-up visits, initial assessments, creating and updating medical records, providing continuity of care with the providing of information to primary care providers, faxing and/or other communications to interested parties (e.g., medical directors).

Certain preferred embodiments of this invention comprise an apparatus for conducting healthcare examinations of patients that are at a site. The apparatus is operated by an operator that has been trained to use the apparatus. The operator preferably is a healthcare professional, such as a skilled nurse.

The apparatus of these preferred embodiments has a number of components. These components comprise (a) a self-contained mobile workstation that is operated by the operator. These embodiments may have wheels to make them portable and easily movable to, for example, different rooms or bedside or different locations. These embodiments also comprise (b) a computing device comprising a CPU, storage, and a keyboard, that is preferably a laptop computer, although other computers can be used, such as tablets and desktop computers. The computing device is located on the workstation and it is operated by the operator.

These preferred embodiments also comprise (c) a plurality of monitors (e.g., two) located on the workstation and connected to the computing device for viewing by the operator. One monitor may be connected to some devices and the other monitor to different devices. Or one monitor may be connected to video, and the other monitor to different devices. These preferred embodiments also have (d) a plurality of cameras located on the workstation and connected to the computing device. The cameras collect video and/or audio from the examinations in real time, although the information may be stored and viewed at other times. These embodiments also have a number of devices connected to them.

These can include (e) a point of care ultrasound machine located on the workstation and connected to the computing device and operated by the operator; (f) a 12 lead EKG unit located on the workstation and connected to the computing device and operated by the operator; (g) an otoscope located on the workstation and connected to the computing device and operated by the operator; (h) a thermometer located on the workstation and connected to the computing device and operated by the operator; (i) a blood glucose machine located on the workstation and connected to the computing device and operated by the operator; (j) a pulse oximeter located on the workstation and connected to the computing device and operated by the operator; (k) a blood pressure cuff located on the workstation and connected to the computing device and operated by the operator; and (l) a stethoscope located on the workstation and connected to the computing device and operated by the operator. Other devices can by connected depending on the needs of the particular patients, disease states, and/or healthcare providers. These devices are connected to the computing device by (m) cables and/or wireless connections.

With these preferred embodiments, the examinations of the patients comprise remote and virtual examinations by one or more healthcare providers who are not located on site viewing and/or hearing the video and/or audio in real time provided by the plurality of cameras. The examinations also comprise the healthcare providers who are not located on site viewing information about the patients from the ultrasound machine, the EKG, the otoscope, the thermometer, the blood glucose machine, the pulse oximeter, the blood pressure cuff, and the stethoscope. Some examinations may not use all of this information (e.g., an ultrasound may not be collected, but it is capable of being collected). In addition, to the healthcare providers, other interested persons can view and/or hear the video and/or audio from the plurality of cameras in real time.

Other preferred embodiments of this invention comprise a method of conducting virtual healthcare examinations of patients who are at a site. These embodiments comprise (a) providing video and/or audio from the examinations of the patients to one or more healthcare providers who are not located on site from a plurality of cameras located on a self-contained mobile workstation and connected to a computer device comprising a CPU, storage and a keyboard (e.g., a laptop computer). These embodiments also comprise (b) providing the video and/or audio from the examinations of the patients to other persons interested in the healthcare of the patients who are not located on site, and (c) gathering patient information from the patients from a plurality of devices, the plurality of devices comprising an ultrasound machine, a 12 lead EKG unit, an otoscope, a thermometer, a blood glucose machine, a pulse oximeter, a blood pressure cuff, and a stethoscope, wherein the plurality of devices are located on or in the workstation and are connected to the computer device by wired and/or wireless connections. These embodiments also comprise (d) providing the patent information from the plurality of devices to the computer device through the wired and/or wireless connections; and (e) providing the patient information from the computer device to the one or more healthcare providers who are not located on site, and the other persons who are not located on site, over a network.

Other preferred embodiments of this invention include a system for providing remote and virtual examinations of patients using multiple apparatus (such as a plurality of the preferred apparatus embodiments described above) and the methods described herein (such as the preferred method embodiments described above).

Embodiments of this invention solve the problem of skilled nursing facilities and rural areas, among others, that do not have the appropriate tools or equipment to get this type of diagnostic testing and send it to other healthcare providers, such as residents in an emergency room. Similarly, embodiments of this invention solve the problem of traditional telemedicine that also does not allow for healthcare providers to get this type of diagnostic information to definitively treat a patient in-house. Additional benefits of this invention will be apparent to a person of skill in the art reading this application.

DETAILED DESCRIPTION OF THE INVENTION

Figure 1:
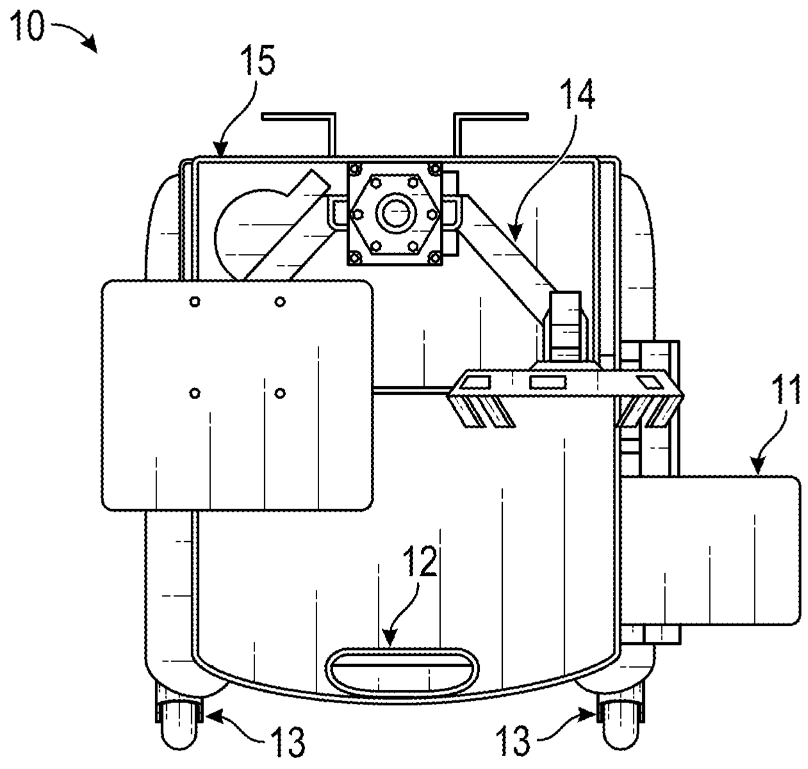
FIG. 1 is a top down view of an embodiment of an apparatus of this invention.

Telemedicine has been a buzzword in the medical field for some years now, and its importance became apparent not only during the COVID-19 pandemic, but even more so after. But as with many things created out of necessity, it has it downfalls.

Traditionally, telemedicine has been a phone call or a video conference with a patient without any way to deliver and determine crucial information. Standard vital signs can be given, but the real diagnostic testing that may be needed has never really been utilized. In certain embodiments of this invention, technology and medical providers come together to form a complete virtual care system, definitive medical testing and diagnostics can be done.

Embodiments of this invention can be used to provide virtual care, which takes the quality-of-care deliverable from telemedicine to a whole new level. Virtual care is remote medicine, consultations, and other virtual healthcare services like 12 lead EKG's, point of care ultrasound imaging, blood labs, and more, all done instantly and at bedside. This type of virtual care enables healthcare providers to connect with patients through online portals, video conferencing, and mobile technologies. This means that healthcare providers can connect with patients, assess them, get definitive diagnostics, and accurately care and prescribe medication without being physically present and without unneeded transport to ER's and other medical facilities. This service can be valuable to many industries, especially long-term care.

Long-term care facilities, such as nursing homes and assisted living centers, often face a shortage of staff. This can be due to several reasons, low wages, inadequate training, and education, among others. For facilities, this can lead to burnout, increased call outs, open shifts, increased penalties, lower matrix scores and lower census. More importantly however, for residents, this can lead to a decreased quality of care and poor health outcomes. Proper virtual care provided by embodiments of this invention solves these challenges.

Advantages of this invention include, one, that it can drastically reduce the number of physical visits that residents need to make to hospitals or clinics, as well as cut down if not eliminate 30-day readmissions, which can be time-consuming and costly.

Two, the virtual care of this invention can assist in monitoring residents' health conditions. For example, remote patient monitoring technologies can monitor vital signs such as blood pressure, heart rate, or oxygen levels and alert staff to any significant changes, allowing them to act promptly.

Three, the virtual care of this invention can provide more specialized care, particularly in regions where staffing shortages limit access to sub-specialized medical professionals. Through virtual consultations, residents can consult with specialists from different parts of the country, exponentially expanding the talent pool available to, for example, long term care facilities.

Four, the virtual care of this invention can offer behavioral health evaluations, which can be challenging to provide due to the shortage of behavioral healthcare providers.

Fifth, the virtual care of this invention can greatly impact and decrease the workload of staff already struggling to keep up with a resident's care.

By creating 24/7 access to healthcare providers, there can be a dramatic decrease in charting times, time waiting for call backs from primary care providers or on call healthcare providers, and more importantly, the time savings of catching an issue early on before it becomes a life challenging situation requiring immediate attention and taking staff away from other duties for a long period of time. The addition of a "virtual staff" available to address all aspects of medical care immediately, can save hours of time for nurses.

The virtual care of this invention can help long-term care facilities address some of the staffing challenges they face while improving residents' well-being, increasing staff efficiency, and promoting cost-savings. Because the long-term healthcare industry continues to evolve and adapt to new technologies, the virtual care of this invention is an essential tool for healthcare providers and facilities and will become the standard of care for senior health.

In particular, certain embodiments of this invention provide healthcare in skilled nursing facilities and rural areas, or any other area where a virtual health care connection can increase the quality of care for patients. These embodiments enable healthcare providers to have a full virtual and audio connection with not only patients, but also staff in skilled nursing and other facilities or locations, as well as family members of patients, and other interested persons.

These embodiments comprise a virtual healthcare apparatus that is self-contained and it comprises at least two video monitors and a laptop or other computer, connected with one another, preferably on the top. One monitor is used for virtual connections to other healthcare staff and connections to equipment such as an otoscope, a Bluetooth stethoscope, as well as additional virtual cameras allowing healthcare providers an accurate and high-definition view of the patient, surroundings, and any type of examination that may be conducted.

The second monitor is used for a portable 12-lead EKG (or ECG) machine and also point of care ultrasound units. This second monitor is integrated into the apparatus' system and it the information displayed can also be seen on the apparatus' top laptop as well as by other healthcare providers located virtually, all in real-time. This enables the healthcare providers to provide a full and complete comprehensive emergency room exam (or other exam) in the room where the apparatus is located.

The virtual healthcare providers connected to the apparatus are then able to work with the person, such as a healthcare provider, on site at the apparatus (e.g., skilled nursing staff) to deliver a full and comprehensive emergency room exam (or other exam), eliminating the need for senior residence and skilled nursing facilities or other facilities or locations to send the patient to the emergency room or other facility. It can also eliminate or reduce the prevalence or need for 30 day readmissions.

In addition to the connections described above, the apparatus has the ability to connect with other third party products. In some embodiments, this can include the ability to do comprehensive metabolic panels and other laboratory blood testing associated with the exam being conducted.

The apparatus can also have family members, personal healthcare providers, and other interested persons connect virtually into the exam through a sent link, allowing them to be present and speak directly to healthcare providers and ask any questions regarding care and treatment of the patient.

In preferred embodiments, the apparatus can accommodate up to 10 additional virtual cameras allowing for full views of the patient, any wounds, skin irritations, marks, bruises, or areas of swelling or concern.

In preferred embodiments, the 12 lead EKG (or ECG) is able to produce an FDA-approved hospital grade 12 lead EKG, which is then stored electronically and which can also be printed directly at the facility on site, or sent to interested person off site. Thus, the apparatus may have one or more printers and/or connect to such wirelessly or by wire on site.

In preferred embodiments, the apparatus' point of care ultrasound unit can deliver cardiac, vascular, lung, musculoskeletal, nerves, ophthalmic, neo head, small part, abdominal obgyn and other scans.

In preferred embodiments, the apparatus can also integrate with other healthcare provider electronic systems (e.g., EMRS) for direct transmission of patient charts and information.

The apparatus allows for healthcare providers to actually treat a patient in the facility by utilizing tools in definitive medical diagnostic care. It allows healthcare providers to have a full picture of the patient with imaging, EKG's, and blood work, with all the results that a patient would normally need to go to the emergency room to receive. Skilled nursing facilities do not have the appropriate tools or equipment to get this type of diagnostic testing in the past and required the patients to be sent to an emergency room or other facility. Traditional tele-medicine does not allow for providers to get this type of diagnostic information to definitively treat a patient in-house.

While interactions with respect to particular devices were discussed above, other connections (e.g., to different monitors) are possible and one of skill in the art will understand the various ways the devices can be connected to one another in a manner tailored to the particular needs of the patients or location, or the desires of the healthcare staff.

Advantages from certain embodiments of his invention include increased access to medical healthcare providers, specialists and improved emergency telemedicine, based upon state-of-the-art remote diagnostic technology. This may result in a dramatic decrease in unnecessary patient transports and 30-day readmissions and associated costs. The apparatus and system of this invention increases the quality and speed of resident care and comfort while minimizing stress, risks of exposure to infectious diseases (COVID-19, colds, flu, etc.), and risks of slips, trips and falls when traveling. They can also be customized to specific needs and can elevate a staff's overall capabilities.

An embodiment of an apparatus of this invention is shown in FIGS. 1-4. FIG. 1 is a top down view of this embodiment 10, showing a mouse tray 11 that slides into place for use, a built in handle 12 for moving the apparatus, caster wheels 13, also for moving the apparatus, an open space 14 for placing objects and charts, and an accessory bin 15, also for placing objects.

Figure 2:
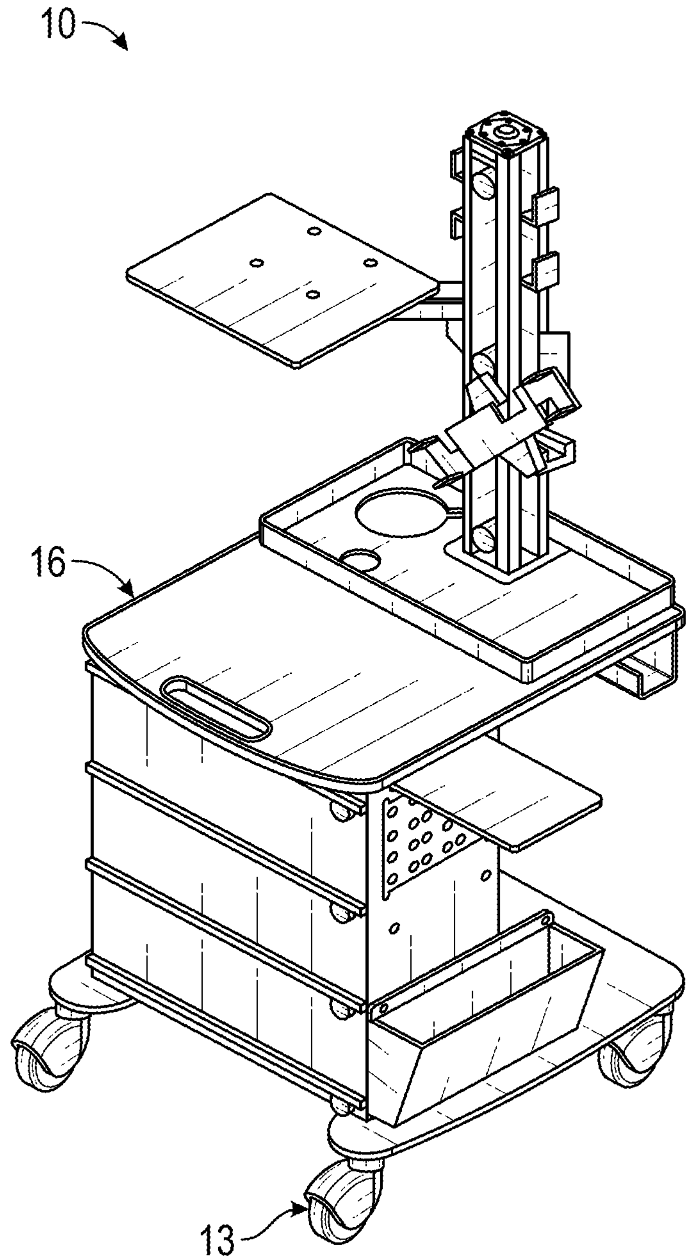
FIG. 2 is a perspective view of an embodiment of an apparatus of this invention.

FIG. 2 is a perspective view of an embodiment of an apparatus 10 of this invention. It illustrates the caster wheels 13, as well as a work surface (e.g., thermofoil material that is durable).

Figure 3:
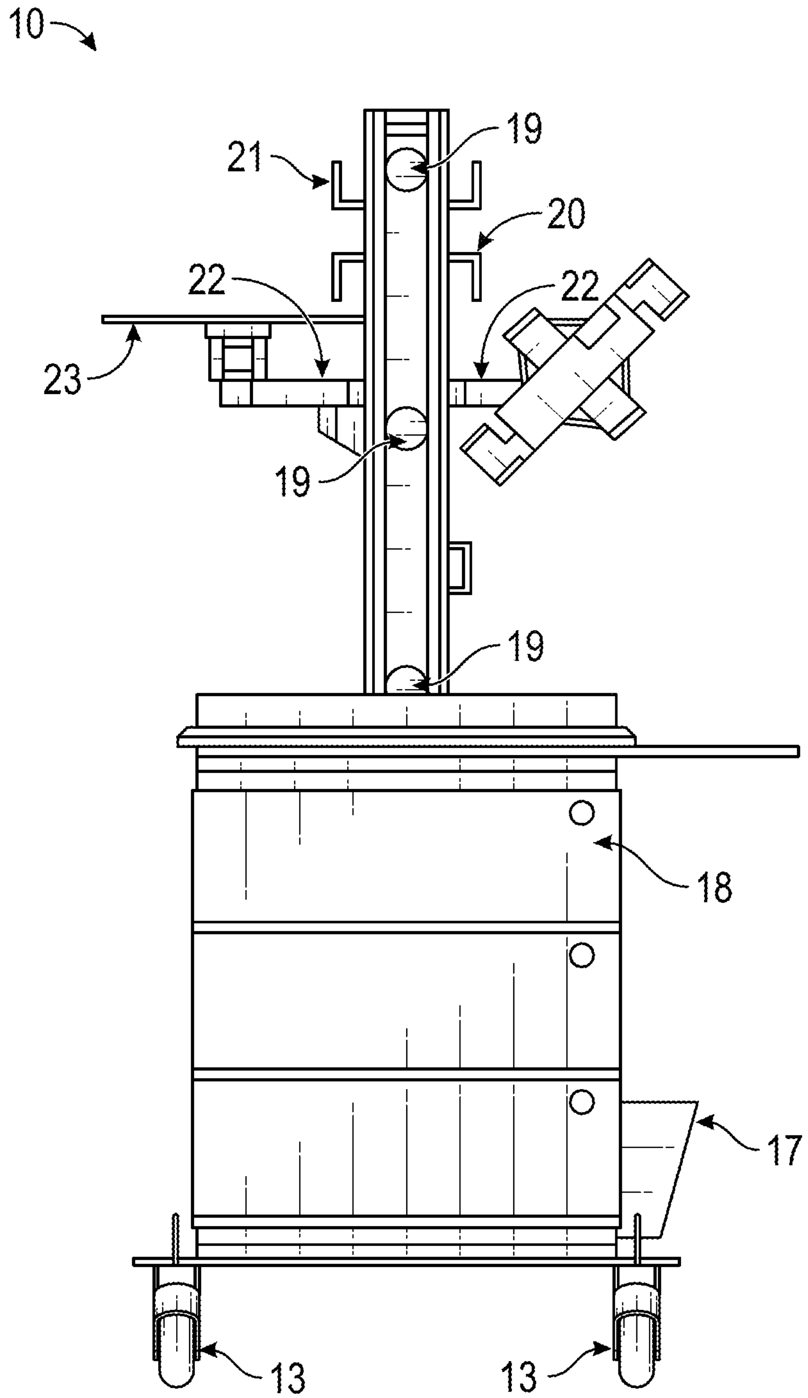
FIG. 3 is a front view of an embodiment of an apparatus of this invention.

FIG. 3 is a front view of an embodiment of an apparatus 10 of this invention. It illustrates the caster wheels 13, a binder holder 17, drawers 18, cable grommets 19, cord wraps 20, 21, extension arms 22, and a laptop plate 23.

Figure 4:
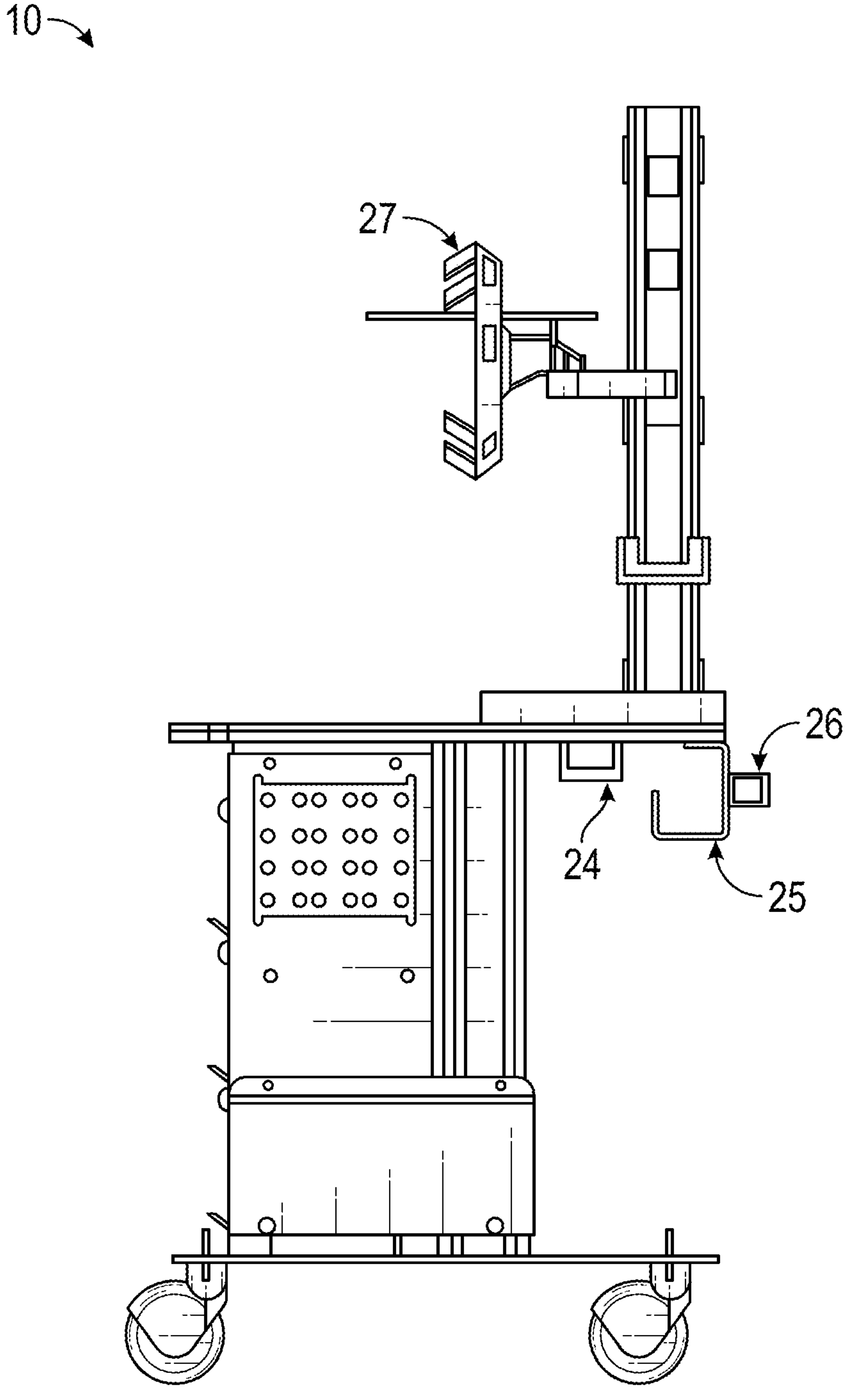
FIG. 4 is a side view of an embodiment of an apparatus of this invention.

FIG. 4 is a side view of an embodiment of an apparatus 10 of this invention. It illustrates a power strip 24, a cable management holder 25, a cord wrap 26 and a lockable tablet holder 27.

The particular devices that are integrated with the apparatus can be stored and/or located, on or in the apparatus. These include the monitors, a computer, an ultrasound machine, a 12 lead EKG unit, one or more cameras, a wired and/or wireless WIFI connection, a Bluetooth connection, an otoscope, a thermometer, a blood glucose machine, a pulse oximeter, a blood pressure cuff, a Bluetooth/WIFI stethoscope, among others, along with connecting cords and wires. Some of these individual devices may themselves be integrated in a vitals machine, which communicates with the apparatus, and which is stored on or in the apparatus.

Example 1

In this example an embodiment of a mobile virtual healthcare apparatus and system is provided in a compact, self-contained and moveable workstation. The apparatus may get its electrical connectivity from a cord and service from a wall outlet and/or batteries. It may include a CPU that runs software applications and provides for the storage and communication of data and other information.

The components of the apparatus comprise at least two monitors (e.g., tablets) connected to the system, that has wireless and/or other internet connectivity. It may also have local network connectivity.

The system interfaces with various devices and applications for point of care ultrasound (e.g., handheld, such as a Vave handheld wireless ultrasound) and a 12 lead EKG unit (e.g., Kardioscreen).

The system also interfaces with one or more cameras and a virtual telemedicine connection that can connect up to 10 additional users (e.g., other healthcare professionals, including specialists, family members, other interested persons). All of these individuals can communicate through the system with each other. However, there may be muting and privacy selections that limit certain of the people who are communicating at certain times. The system can save and communicate information collected from the participants to the other participants and to centralized repositories or other interested persons, as well as the devices it interfaces with.

The system also interfaces with vital sign machines, such as an otoscope, a thermometer, a blood glucose machine, a pulse oximeter (e.g., to obtain a SpO2 reading), a blood pressure cuff, and a Bluetooth/WIFI stethoscope for the auscultation of lung and heart sounds, which each may be handheld and be connected directly to the apparatus or a component of the apparatus (e.g., a monitor or CPU). Additional devices may be added to provide for particular capabilities in a given clinical setting (e.g., specific devices for specific patients or disease states).

OTHER EMBODIMENTS

Although the present invention has been described with reference to teaching, examples and preferred embodiments, one skilled in the art can easily ascertain its essential characteristics, and without departing from the spirit and scope thereof can make various changes and modifications of the invention to adapt it to various usages and conditions. Those skilled in the art will recognize or be able to ascertain using no more than routine experimentation, many equivalents to the specific embodiments of the invention described herein. Such equivalents are encompassed by the scope of the present invention.

What is claimed is:

1. A workstation for conducting healthcare examinations, the workstation comprising:
   - a local computing device;
   - one or more monitors communicatively coupled with the local computing device;
   - one or more cameras communicatively coupled with the local computing device;
   - a plurality of medical equipment communicatively coupled with the local computing device; and
   - a communication interface communicatively coupled with the local computing device and configured to enable communications between the local computing device and a remote computing device,
   - wherein the workstation enables an operator to conduct a healthcare examination on a patient using the medical equipment, the one or more cameras and the one or more monitors and the local computing device is configured to provide patient information of the healthcare examination to the remote computing device via the communication interface, and
   - wherein the workstation is local to the operator and the patient, and the remote computing device is not local to the workstation.

2. The workstation of claim 1, wherein the workstation further comprises wheels coupled with the workstation thereby making the workstation portable.

3. The workstation of claim 1, wherein the plurality of medical equipment comprises at least one of a blood pressure cuff, a pulse oximeter, an electrocardiography unit, an ultrasound transducer, a thermometer, a glucose meter, a stethoscope, or any combination thereof.

4. The workstation of claim 3, wherein the stethoscope is communicatively coupled with the local computing device via Bluetooth or WiFi.

5. The workstation of claim 1, wherein the local computing device is configured to store the patient information, imagery and/or audio in an electronic medical record associated with the patient.

6. The workstation of claim 1, wherein the local computing device is configured to provide video, audio and/or patient information to the remote computing device.

7. The workstation of claim 1, wherein the communication interface is configured to enable two-way audio communication between the local computing device and the remote computing device.

8. The workstation of claim 1, wherein the local operator is a nurse and a remote operator is a healthcare professional.

9. A method for providing virtual healthcare, the method comprising:
   - providing a workstation for conducting healthcare examinations proximate to a patient, the workstation comprising a local computing device, one or more monitors communicatively coupled with the local computing device, one or more cameras communicatively coupled with the local computing device, a plurality of medical equipment communicatively coupled with the local computing device, and a communication interface communicatively coupled with the local computing device and configured to enable communications between the local computing device and a remote computing device;
   - conducting, by an operator, a healthcare examination of the patient using the medical equipment, the one or more cameras and the one or more monitors; and
   - communicating, by the local computing device and via the communication interface, patient information of the healthcare examination to the remote computing device,
   - wherein the workstation is local to the operator and the patient, and the remote computing device is not local to the workstation.

10. The method of claim 9, wherein providing the workstation further comprising moving the workstation proximate to the patient via wheels coupled with the workstation.

11. The method of claim 9, wherein conducting the healthcare examination comprises using at least one of a blood pressure cuff, a pulse oximeter, an electrocardiography unit, an ultrasound transducer, a thermometer, a glucose meter, a stethoscope, or any combination thereof.

12. The method of claim 11, further comprising transmitting audio from the stethoscope to the local computing device via Bluetooth or WiFi.

13. The method of claim 9, further comprising storing, by the local computing device, patient information, imagery and/or audio in an electronic medical record associated with the patient.

14. The method of claim 9, wherein communicating the patient information of the healthcare examination to the remote computing device comprises communicating video, audio and/or patient information to the remote computing device.

15. The method of claim 9, further comprising communicating, via the communication interface, two-way audio communication between the local computing device and the remote computing device.

16. The method of claim 9, wherein the local operator is a nurse and a remote operator is a healthcare professional.

17. A distributed virtual healthcare system, the system comprising:

a workstation comprising:

a local computing device;

one or more monitors communicatively coupled with the local computing device;

one or more cameras communicatively coupled with the local computing device;

a plurality of medical equipment communicatively coupled with the local computing device;

a communication interface communicatively coupled with the local computing device and configured to enable communications between the local computing device and a remote computing device; and the remote computing device, wherein the workstation enables an operator to conduct a healthcare examination on a patient using the medical equipment, one or more cameras and the one or more monitors and the local computing device is configured to provide patient information of the healthcare examination to the remote computing device via the communication interface, and wherein the workstation is local to the operator and the patient, and the remote computing device is not local to the workstation.

18. The distributed virtual healthcare system of claim 17, wherein conducting the plurality of medical equipment comprises at least two of a blood pressure cuff, a pulse oximeter, an electrocardiography unit, an ultrasound transducer, a thermometer, a glucose meter, a stethoscope, or any combination thereof.

19. The distributed virtual healthcare system of claim 18, further wherein the communication interface enables two-way audio communication between the local computing device and the remote computing device.

20. The distributed virtual healthcare system of claim 17, wherein the local operator is a nurse and a remote operator is a healthcare professional.

* * * * *